(12) United States Patent
Ishikawa et al.

(10) Patent No.: US 11,390,693 B2
(45) Date of Patent: Jul. 19, 2022

(54) PENTOSAN POLYSULFATE AND METHOD FOR PRODUCING PENTOSAN POLYSULFATE

(71) Applicant: OJI HOLDINGS CORPORATION, Tokyo (JP)

(72) Inventors: Kotaro Ishikawa, Tokyo (JP); Takuro Kashiwamura, Tokyo (JP); Takuya Kato, Tokyo (JP); Toru Koga, Tokyo (JP); Suguru Ishikawa, Tokyo (JP)

(73) Assignee: OJI HOLDINGS CORPORATION, Tokyo (JP)

( * ) Notice: Subject to any disclaimer, the term of this patent is extended or adjusted under 35 U.S.C. 154(b) by 0 days.

(21) Appl. No.: 16/646,243

(22) PCT Filed: Sep. 11, 2018

(86) PCT No.: PCT/JP2018/033535
§ 371 (c)(1),
(2) Date: Mar. 11, 2020

(87) PCT Pub. No.: WO2019/054344
PCT Pub. Date: Mar. 21, 2019

(65) Prior Publication Data
US 2020/0270372 A1    Aug. 27, 2020

(30) Foreign Application Priority Data

Sep. 12, 2017 (JP) .............................. JP2017-175133

(51) Int. Cl.
C08B 37/00 (2006.01)

(52) U.S. Cl.
CPC ...... *C08B 37/0057* (2013.01); *C08B 37/0003* (2013.01)

(58) Field of Classification Search
CPC ................................................. C08B 37/0057
See application file for complete search history.

(56) References Cited

U.S. PATENT DOCUMENTS

| | | | |
|---|---|---|---|
| 4,168,742 A | 9/1979 | Kluppel et al. | |
| 4,699,900 A | 10/1987 | Bayol et al. | |
| 4,713,373 A | 12/1987 | Bayol et al. | |
| 4,727,063 A | 2/1988 | Naggi et al. | |
| 5,516,765 A | 5/1996 | Andermann | |
| 7,902,158 B2 | 3/2011 | Kuszmann et al. | |
| 8,987,216 B2 | 3/2015 | Kuszmann et al. | |
| 8,993,536 B2 | 3/2015 | Kakehi et al. | |
| 2001/0005720 A1 | 6/2001 | Striker et al. | |
| 2003/0109491 A1 | 6/2003 | Ulmer et al. | |
| 2006/0194759 A1 | 8/2006 | Eidelson | |
| 2007/0281893 A1 | 12/2007 | Kuszmann et al. | |
| 2008/0249298 A1 | 10/2008 | Ulmer et al. | |
| 2010/0055060 A1 | 3/2010 | Yoshida et al. | |
| 2010/0261807 A1 | 10/2010 | Laine et al. | |
| 2011/0118198 A1 | 5/2011 | Kuszmann et al. | |
| 2011/0251154 A1 | 10/2011 | Stajic et al. | |
| 2011/0281819 A1 | 11/2011 | Kakehi et al. | |
| 2011/0306567 A1 | 12/2011 | Schofield et al. | |
| 2020/0062867 A1 | 2/2020 | Ishikawa et al. | |

FOREIGN PATENT DOCUMENTS

| | | |
|---|---|---|
| CA | 2018133 A1 | 12/1990 |
| CN | 1051564 A | 5/1991 |
| CN | 1832966 A | 9/2006 |
| CN | 101014607 A | 8/2007 |
| CN | 102061323 A | 5/2011 |
| CN | 102300870 A | 12/2011 |
| CN | 102766225 A | 11/2012 |
| CN | 103320548 A | 9/2013 |
| CN | 105907896 A | 8/2016 |
| CN | 106832020 A | 6/2017 |

(Continued)

OTHER PUBLICATIONS

Daus et al., Macromol. Mater. Eng., 2011, 296, p. 551-561. (Year: 2011).*
"Technology of Wood Chemicals", CMC Publishing Co., Ltd., 2007, p. 108.
Koshijima, "Recent Problems of Hemicellulose Chemistry", Material, 1967, vol. 16, pp. 758-764.
International Preliminary Report on Patentability for PCT/JP2018/007138 dated Oct. 24, 2018, corresponding to U.S. Appl. No. 16/489,074.
International Search Report for PCT/JP2018/007138 dated Mar. 27, 2018, corresponding to U.S. Appl. No. 16/489,074.

(Continued)

*Primary Examiner* — Jonathan S Lau
(74) *Attorney, Agent, or Firm* — Sughrue Mion, PLLC (57) ABSTRACT

The present invention provides a pentosan polysulfate having a uronic acid content of 0.0% by mass to 6.0% by mass, preferably a pentosan polysulfate having a structure represented by Formula I:

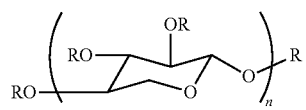

wherein each R represents a hydrogen atom, —COCH$_3$ or —SO$_3$X, and at least one R represents —SO$_3$X, wherein X represents a hydrogen atom or a monovalent or divalent metal, and n represents an integer of 1 or more and 30 or less; a pharmaceutically acceptable salt thereof; or a pharmaceutically acceptable solvate of the pentosan polysulfate or of a pharmaceutically acceptable salt thereof. The present invention further provides a method for producing pentosan polysulfate, the method comprising the steps of depolymerizing a plant-derived raw material to obtain neutral xylooligosaccharide and sulfating the neutral xylooligosaccharide, in this order.

12 Claims, 3 Drawing Sheets

(56) References Cited

FOREIGN PATENT DOCUMENTS

| | | |
|---|---|---|
| EP | 0889055 A1 | 7/1999 |
| ER | 0 116 801 B1 | 4/1987 |
| JP | S48-043100 B1 | 12/1973 |
| JP | S60-063203 A | 4/1985 |
| JP | S61-130301 A | 6/1986 |
| JP | S61-130302 A | 6/1986 |
| JP | S61-197601 A | 9/1986 |
| JP | S62-004362 B2 | 1/1987 |
| JP | H03-20225 A | 1/1991 |
| JP | H09-509650 A | 9/1997 |
| JP | H10-195107 A | 7/1998 |
| JP | H11-049802 A | 2/1999 |
| JP | H11-180821 A | 7/1999 |
| JP | 2003-183303 A | 7/2003 |
| JP | 2003-221307 A | 8/2003 |
| JP | 2003-221339 A | 8/2003 |
| JP | 2004-513185 A | 4/2004 |
| JP | 2005-501931 A | 1/2005 |
| JP | 2009-196915 A | 9/2009 |
| JP | 2009-532467 A | 9/2009 |
| JP | 2013-177433 A | 9/2013 |
| JP | 2014-129383 A | 7/2014 |
| JP | 2015-038061 A | 2/2015 |
| JP | 2016-514090 A | 5/2016 |
| JP | 6225321 B1 | 11/2017 |
| JP | 6281659 B1 | 2/2018 |
| WO | 1991/016058 A1 | 10/1991 |
| WO | 1995/014491 A3 | 6/1995 |
| WO | 1995/014492 A2 | 6/1995 |
| WO | 1998/006409 A2 | 2/1998 |
| WO | 02/041901 A1 | 5/2002 |
| WO | 2005/014656 A1 | 2/2005 |
| WO | 2005/117912 A1 | 12/2005 |
| WO | 2007/014155 A2 | 2/2007 |
| WO | 2007/123800 | 11/2007 |
| WO | 2007/138263 A1 | 12/2007 |
| WO | 2008/107906 A1 | 9/2008 |
| WO | 2009/087581 A1 | 7/2009 |
| WO | 2010/000013 A1 | 1/2010 |
| WO | 2010/089617 A2 | 8/2010 |
| WO | 2010/089617 A3 | 8/2010 |
| WO | 2012/101544 A1 | 8/2012 |
| WO | 2012/114349 A1 | 8/2012 |
| WO | 2013/186857 A1 | 12/2013 |
| WO | 2014/114723 A1 | 7/2014 |
| WO | 2014/122251 A2 | 8/2014 |
| WO | 2014/122251 A3 | 8/2014 |
| WO | 2016/184887 A1 | 11/2016 |
| WO | 2016/191698 A1 | 12/2016 |
| WO | 2018/043667 A1 | 3/2018 |
| WO | 2018/043668 A1 | 3/2018 |

OTHER PUBLICATIONS

Ishihara et al., "Isolation of Xylan from Hardwood by Alkali Extraction and Steam Treatment", Mokuzai Gakkaishi, Journal of Wood Science 1996, vol. 42, No. 12, pp. 1211-1220 (11 pages total).

Kabel et al., "Hydrothermally treated xylan rich by-products yield different classes of xylo-oligosaccharides" Carbohydrate Polymers, 2002, vol. 50, No. 1, pp. 47-56.

Kabel et al., "Complex xylo-oligosaccharides identified from hydrothermally treated Eucalyptus wood and brewery's spent grain", Carbohydrate Polymers, 2002, vol. 50, No. 2, pp. 191-200.

Koutaniemi et al., "Distinct roles of carbohydrate esterase family CE16 acetyl esterases and polymeracting acetyl xylan esterases in xylan deacetylation" Journal of Biotechnology, 2013, vol. 168, No. 4, pp. 684-692.

Pawar et al., "Acetylation of woody lignocellulose: significance and regulation" Frontiers in Plant Science, 2013, vol. 4, No. 118, pp. 1-8.

International Search Report for PCT/JP2017/031434 dated Oct. 31, 2017 corresponding to U.S. Appl. No. 16/643,265.

Office Action issued by the Japanese Patent Office dated Apr. 18, 2017 in JP Application No. 2017-040067.

Office Action issued by the Japanese Patent Office dated Oct. 3, 2017 in JP Application No. 2017-166559.

Moure et al., "Advances in the manufacture, purification and applications of xylo-oligosaccharides as food additives and nutraceuticals", Process Biochemistry, 2006, vol. 41, Issue 9, pp. 1913-1923.

Gullón et al., "Structural features and properties of soluble products derived from *Eucalyptus globulus* hemicelluloses" Food Chemistry, 2011, vol. 127, No. 4, pp. 1798-1807.

Gullón et al., "Membrane processing of liquors from *Eucalyptus globulus* autohydrolysis" Journal of Food Engineering, 2008, vol. 87, No. 2, pp. 257-265.

Ishikawa et al., "Research and development of sulphated hemicellulose (PPS)", The 62nd Japan Technical Association of the Pulp and Paper Industry Annual Meeting, 2019, pp. 1-5.

Scully et al., "The antiheparin effect of a heparinoid, pentosane polysulphate" Biochem. J, 1984, vol. 218, pp. 657-665.

McCarty et al., "Sulfated glycosaminoglycans and glucosamine may synergize in promoting synovial hyaluronic acid synthesis" Medical Hypotheses, 2000, vol. 54, No. 5, pp. 798-802.

Ferrao et al., "The effect of heparin on cell proliferation and type-I collagen synthesis by adult human dermal fibroblasts" Biochimica et Biophysica Acta, 1993, vol. 1180, pp. 225-230.

International Search Report for PCT/JP2018/020644 dated Sep. 4, 2018, corresponding to U.S. Appl. No. 16/617,783.

International Search Report for PCT/JP2017/031433 dated Oct. 31, 2017 corresponding to U.S. Appl. No. 16/643,215.

Office Action issued by the Japanese Patent Office dated Jan. 8, 2019 in JP Application No. 2018-553269.

Office Action issued by the Japanese Patent Office dated Feb. 5, 2019 in JP Application No. 2018-229611.

Hirst et al., "Water-soluble Polysaccharides of Cladophora" Journal of the Chemical Society, 1965, pp. 2958-2967.

International Search Report for PCT/JP2018/033535 dated Nov. 27, 2018 corresponding to the present application.

International Search Report for PCT/JP2018/046537 dated Mar. 5, 2019.

International Search Report for PCT/JP2017/031432 dated Oct. 31, 2017.

Office Action issued by the Japanese Patent Office dated Jul. 17, 2019 in JP Application No. 2018-516078.

Office Action issued by the Japanese Patent Office dated Jul. 17, 2019 in JP Application No. 2018-516079.

Gonzalez et al., "Demonstration of Inhibitory Effect of Oral Shark Cartilage on Basic Fibroblast Growth Factor-Induced Angiogenesis in the Rabbit Cornea" Biol. Pharm. Bull, 2001, vol. 24, No. 2, pp. 151-154.

Swain et al., "Heparin-Binding Growth Factor Blockade with Pentosan Polysulfate" Annals of the New York Academy of Sciences, 1993, vol. 698, pp. 63-70.

Zugmaier et al., "Polysulfated Heparinoids Selectively Inactivate Heparin-Binding Angiogenesis Factors" Annals of the New York Academy of Sciences, 1999, vol. 886, pp. 243-248.

Zugmaier et al., "Inhibition by Pentosan Polysulfate (PPS) of Heparin-Binding Growth Factors Released From Tumor Cells and Blockage by PPS of Tumor Growth in Animals" Journal of the National Cancer Institute, 1992, vol. 84, No. 22, pp. 1716-1724.

Garrote et al., "Non-isothermal autohydrolysis of *Eucalyptus* wood", Wood Science and Technology, 2002, vol. 36, pp. 111-123.

Sivová et al., "Fagus sylvatica glucuronoxylan sulfate-chemical profile and pharmacological view" Starch, 2015, vol. 68, pp. 621-628.

Rhee et al., "Engineering the Xylan Utilization System in Bacillus subtilis for Production of Acidic Xylooligosaccharides" Applied and Environmental Microbiology, 2014, vol. 80, No. 3, pp. 917-927.

Maekawa et al., "Infrared Spectra of Wood Cellulose and Related Polysaccharide" Kyoto University, Research Institute Report, 1968, vol. 43, pp. 1-8.

Kabel et al., "In Vitro Fermentability of Differently Substituted Xylo-oligosaccharides", Journal of Agricultural and Food Chemistry, 2002, vol. 50, pp. 6205-6210.

Office Action issued by Japanese Patent Office dated Oct. 9, 2018 in JP Application No. 2018-516078.

(56) References Cited

OTHER PUBLICATIONS

International Preliminary Report on Patentability dated Dec. 3, 2019 from the International Bureau in International Application No. PCT/JP2018/020644, corresponding to U.S. Appl. No. 16/617,783.
Office Action dated Nov. 16, 2020 in Australian Application No. 2018276567.
Stephen Dealler et al., "Pentosan polysulfate as a prophylactic and therapeutic agent against prion disease", IDrugs, vol. 6, No. 5, Jun. 1, 2003, pp. 470-478, XP055777416 (10 pages total).
Extended European Search Report dated Feb. 26, 2021 from the European Patent Office in EP Application No. 17846672.8, corresponding to U.S. Appl. No. 16/643,265.
Takayuki Ohbuchi et al., "Structural Analysis of Neutral and Acidic Xylooligosaccharides from Hardwood Kraft Pulp, and Their Utilization by Intestinal Bacteria in Vitro", Bioscience, Biotechnology, and Biochemistry, vol. 73, No. 9, 2009, pp. 2070-2076 (8 pages total).
Office Action dated Jun. 2, 2021 from the United States Patent and Trademark Office in U.S. Appl. No. 16/643,215.
ELMIRON®—100 MG (Pentosan Polysulfate Sodium) Capsules,2002, https://www.accessdata.fda.gov/drugsatfda_docs/label/2020/020193s014lbl.pdf (14 pages).
Office Action dated Mar. 25, 2021 issued by the Indian Patent Office in Indian Application No. 201947036653.
Office Action dated Mar. 2, 2021 in U.S. Appl. No. 16/489,074.
Extended European Search Report dated Feb. 3, 2021, from the European Patent Office in EP application No. 18809395.9, corresponding to U.S. Appl. No. 16/617,783.
Communication dated Jan. 4, 2022 from the Indian Patent Office in Indian Application No. 202047029636, corresponding to U.S. Appl. No. 16/955,641.
Office Action dated Oct. 25, 2021 issued by China National Intellectual Property Administration Machine in Chinese Patent Application No. 201880058953.X.
Teleman et al., "Characterization of O-acetyl-(4-O-methylglucurono)xylan isolated from birch and beech", Carbohydrate Research, 2002, vol. 337, pp. 373-377 (5 pages total).
Office Action dated Sep. 17, 2021 by Indian Patent Office in Indian Application No. 202047012044.
Office Action dated Aug. 30, 2021 by China National Intellectual Property Administration in Chinese Application No. 201780094371.2.
Mi et al., "Preparation of corn stover pentosan sulfate", Journal of Changchun University of Technology (Natural Science Edition), 2014, vol. 35, No. 6, pp. 716-719 (4 pages total).
Extended European Search Report dated Sep. 29, 2021 by European Patent Office in European Application No. 18890627.5.
Herbert et al., "Activity of Pentosan Polysulphate and Derived Compounds on Vascular Endothelial Cell Proliferation and Migration Induced by Acidic and Basic FGF In Vitro", Biochemical Pharmacology, 1988, vol. 37, No. 22, pp. 4281-4288 (8 pages total).
Office Action dated Oct. 26, 2021 in U.S. Appl. No. 16/955,641.
Gura, "Cancer Models: Systems for Identifying New Drugs Are Often Faulty", Science, 1997, vol. 278, No. 5340, pp. 1041-1042 (6 pages total).
"The Merck Manual", Sixteenth Edition, 1992, pp. 339-342 and 1488-1490 (6 pages total).
Smith et al., "Cancer, inflammation and the AT1 and AT2 receptors", Journal of Inflammation, 2004, vol. 1, No. 3, pp. 1-12 (12 pages total).
Vergnolle et al., "Protease-activated receptors and inflammatory hyperalgesia", Mem Inst Oswaldo Cruz, Rio de Janeiro, 2005, vol. 100 (Suppl. I), pp. 173-176 (4 pages total).
Douglass et al., "1. Diagnosis, treatment and prevention of allergic disease: the basics", MJA Practice Essentials—Allergy, 2006, vol. 185, No. 4, pp. 228-233 (6 pages total).

* cited by examiner

PENTOSAN POLYSULFATE AND METHOD FOR PRODUCING PENTOSAN POLYSULFATE

CROSS REFERENCE TO RELATED APPLICATIONS

This application is a National Stage of International Application No. PCT/JP2018/033535 filed Sep. 11, 2018, claiming priority based on Japanese Patent Application No. 2017-175133 filed Sep. 12, 2017.

TECHNICAL FIELD

The present invention relates to a pentosan polysulfate, and a method for producing the pentosan polysulfate.

BACKGROUND ART

Heparin has been used as a therapeutic agent for thrombosis, osteoarthritis, and the like. However, since heparin is a substance separated from the organs of animals, such as bovines or pigs, it is difficult to control the quality thereof. Further, there are cases where the use of heparin in treatment causes hesitation from the viewpoint of religious ethics etc. Therefore, the development of an alternative therapeutic agent that is free of animal-derived components, and that can be used instead of heparin, has been desired.

As such an alternative substance for heparin, pentosan polysulfate, for example, is known. Pentosan polysulfate is obtained by sulfating a plant-derived xylooligosaccharide. Since such pentosan polysulfate is a substance free of animal-derived components, its use as an alternative therapeutic agent for heparin has been expected (for example, Patent Literature (PTL) 1).

Pentosan polysulfate is produced by chemical sulfation of xylan obtained from hardwood (e.g., beech). Pentosan polysulfate is composed of a sulfated linear polysaccharide in which β-D-xylopyranose is linearly bonded; and has 4-O-methylglucuronic acid, i.e., uronic acid, per roughly every 10 xylopyranose units (Patent Literature (PTL) 1 and Patent Literature (PTL) 2).

CITATION LIST

Patent Literature

PTL 1: WO2010/000013
PTL 2: JP2009-532467A

SUMMARY OF INVENTION

Technical Problem

An object of the present invention is to provide a novel pentosan polysulfate having activity preferable for pharmaceutical applications, or having storage stability. Another object of the present invention is to provide an inexpensive and efficient method for producing the pentosan sulfate.

Means for Solving the Problem

As a result of intensive studies to solve the above problem, the present inventors found a novel pentosan polysulfate having higher anticoagulant activity than conventional pentosan polysulfates, while suppressing side effects or having storage stability. The present inventors thus accomplished the present invention based on this finding. Specifically, the present invention has the following constitution.

[1] A pentosan polysulfate having a uronic acid content of 0.0 mass % to 6.0 mass %;
a pharmaceutically acceptable salt thereof; or
a pharmaceutically acceptable solvate of the pentosan polysulfate or of a pharmaceutically acceptable salt thereof.
[2] The pentosan polysulfate according to [1], wherein the pentosan polysulfate has a uronic acid content of 0.0 mass % to 4.0 mass %;
a pharmaceutically acceptable salt thereof; or
a pharmaceutically acceptable solvate of the pentosan polysulfate or of a pharmaceutically acceptable salt thereof.
[3] The pentosan polysulfate according to [1] or [2], wherein the pentosan polysulfate has a structure represented by Formula II:

Formula II wherein $R^1$ each independently represents a hydrogen atom, $-COCH_3$, or $-SO_3X^1$, and at least one $R^1$ in the molecule is $-SO_3X^1$, wherein $X^1$ represents a hydrogen atom or a monovalent or divalent metal; n1 and n2 each independently represent an integer of 0 or more and 30 or less, and at least one of n1 and n2 is an integer of 1 or more; and R* represents a hydrogen atom, $-COCH_3$, $-SO_3X^1$, or a sulfated or non-sulfated uronic acid residue;
a pharmaceutically acceptable salt thereof; or
a pharmaceutically acceptable solvate of the pentosan polysulfate or of a pharmaceutically acceptable salt thereof.
[4] The pentosan polysulfate according to any one of [1] to [3], wherein the pentosan polysulfate is represented by Formula Formula I wherein each R independently represents a hydrogen atom, $-COCH_3$ or $-SO_3X$, and at least one R is $-SO_3X$, wherein X represents a hydrogen atom or a monovalent or divalent metal; and n represents an integer of 1 to 30;
a pharmaceutically acceptable salt thereof; or
a pharmaceutically acceptable solvate of the pentosan polysulfate or of a pharmaceutically acceptable salt thereof.
[5] The pentosan polysulfate according to [4], wherein each R independently represents a hydrogen atom or $-SO_3X$;
a pharmaceutically acceptable salt thereof; or
a pharmaceutically acceptable solvate of the pentosan polysulfate or of a pharmaceutically acceptable salt thereof.
[6] The pentosan polysulfate according to [4] or [5], wherein X is sodium;
a pharmaceutically acceptable salt thereof; or
a pharmaceutically acceptable solvate of the pentosan polysulfate or of a pharmaceutically acceptable salt thereof.

[7] A pharmaceutical composition comprising
the pentosan polysulfate according to any one of [1] to [6];
a pharmaceutically acceptable salt thereof; or
a pharmaceutically acceptable solvate of the pentosan polysulfate or of a pharmaceutically acceptable salt thereof.
[8] An anticoagulant comprising
the pentosan polysulfate according to any one of [1] to [6];
a pharmaceutically acceptable salt thereof; or
a pharmaceutically acceptable solvate of the pentosan polysulfate or of a pharmaceutically acceptable salt thereof.
[9] A method for producing pentosan polysulfate comprising:
a first step of obtaining neutral xylooligosaccharide from a plant-derived raw material; and
a second step of obtaining pentosan polysulfate from the neutral xylooligosaccharide,
the first step comprising a step of depolymerizing the plant-derived raw material, and the second step comprising a step of sulfating the neutral xylooligosaccharide.
[10] The method for producing pentosan polysulfate according to [9], wherein the depolymerization step is a heat treatment step.
[11]
The method for producing pentosan polysulfate according to [10], wherein the heat treatment step is a step of heating to 120° C. or higher under non-alkaline conditions.
[12]
The method for producing pentosan polysulfate according to any one of [9] to [11], wherein the plant-derived raw material is a wood-derived raw material.

From another point of view, the present invention provides:
use of pentosan polysulfate according to any one of [1] to [6], a pharmaceutically acceptable salt thereof, or a pharmaceutically acceptable solvate of the pentosan polysulfate or of a pharmaceutically acceptable salt thereof, as an anticoagulant;
use of the pentosan polysulfate according to any one of [1] to [6], a pharmaceutically acceptable salt thereof, or a pharmaceutically acceptable solvate of the pentosan polysulfate, or of a pharmaceutically acceptable salt thereof, for producing an anticoagulant;
the pentosan polysulfate according to any one of [1] to [6], a pharmaceutically acceptable salt thereof, or a pharmaceutically acceptable solvate of the pentosan polysulfate or of a pharmaceutically acceptable salt thereof, for use as an anticoagulant;
a method for inhibiting blood coagulation, comprising administering to a human or an animal a moisturizingly effective amount of the pentosan polysulfate according to any one of [1] to [6], a pharmaceutically acceptable salt thereof, or a pharmaceutically acceptable solvate of the pentosan polysulfate or of a pharmaceutically acceptable salt thereof;
a method for surface-treating a medical device or a medical material, comprising applying to a surface of the medical device or the medical material the pentosan polysulfate according to any one of [1] to [6], a pharmaceutically acceptable salt thereof, or a pharmaceutically acceptable solvate of the pentosan polysulfate or of a pharmaceutically acceptable salt thereof.

Advantageous Effects of Invention

The present invention provides a pentosan polysulfate having an activity preferable for pharmaceutical applications, or having storage stability. The pentosan polysulfate of the present invention is useful as a pharmaceutical composition, such as an anticoagulant. The present invention further provides an inexpensive and efficient method for producing the pentosan polysulfate.

DESCRIPTION OF EMBODIMENTS

The present invention is described below in detail. The constituent features may be described below based on typical embodiments and specific examples; however, the present invention is not limited to such embodiments.

Pentosan Polysulfate

Pentosan polysulfate is a compound obtained by sulfation of at least one hydroxyl group of xylooligosaccharide. In the present specification, pentosan polysulfate includes salts of pentosan polysulfate, solvates of pentosan polysulfate, and solvates of salts of pentosan polysulfate. Salts of pentosan polysulfate are preferably pharmaceutically acceptable salts, and examples include pentosan polysulfate sodium, pentosan polysulfate potassium, pentosan polysulfate calcium, and the like. The solvates are preferably pharmaceutically acceptable solvates. Examples of solvents include water.

Pentosan polysulfate has a structure represented by Formula II. Pentosan polysulfate may contain one structure represented by Formula II, or may contain two or more structures represented by Formula II. When pentosan polysulfate contains two or more structures represented by Formula II, the structure represented by Formula II is a structure representing a repeating unit of pentosan polysulfate.

Formula II

In Formula II, $R^1$ each independently represents a hydrogen atom, —$COCH_3$, or —$SO_3X^1$, and at least one $R^1$ in the molecule is —$SO_3X^1$, wherein $X^1$ represents a hydrogen atom or a monovalent or divalent metal; and $X^1$ is preferably a hydrogen atom, sodium, potassium, or calcium, more preferably sodium, potassium, or calcium, and particularly preferably sodium. Further, n1 and n2 each independently represent an integer of 0 or more and 30 or less, and at least one of n1 and n2 is an integer of 1 or more.

In Formula II, n1+n2 is preferably from 1 to 27, more preferably from 2 to 18, and even more preferably from 3 to 10.

The portion that is an end of the structure represented by Formula II and that does not bind to a structure represented by Formula II may be —OR$^1$. That is, —OR$^1$ may bind to the left terminus (n1 side) of Formula II, whereas —R$^1$ may bind to the right terminus (n2 side) of Formula II. It is particularly preferable that —OR$^{1X}$ binds to the left terminus (n1 side) of Formula II, and —R$^{1X}$ binds to the right terminus (n2 side) of Formula II. In Formula II, R$^{1X}$ is a hydrogen atom or —SO$_3$X$^1$; X$^1$ is a hydrogen atom or a monovalent or divalent metal; and X$^1$ is preferably a hydrogen atom, sodium, potassium, or calcium, more preferably sodium, potassium, or calcium, and particularly preferably sodium.

R* is a hydrogen atom, —COCH$_3$, —SO$_3$X$^1$, or a sulfated or non-sulfated uronic acid residue. The sulfated or non-sulfated uronic acid residue can be represented by the following formula.

Formula I

X$^2$ represents a hydrogen atom or a monovalent or divalent metal; preferably sodium, potassium, or calcium; and particularly preferably sodium. R$^1$ each independently represents a hydrogen atom, —COCH$_3$, or —SO$_3$X$^1$, as described above. * represents a bonding position.

The pentosan polysulfate of the present invention does not include the pentosan polysulfate of Formula II wherein R* is a uronic acid residue, or may possibly contain a small amount of such pentosan polysulfate. Specifically, the pentosan polysulfate of the present invention has a uronic acid content of 0.0 mass % to 6.0 mass %. The pentosan polysulfate of the present invention preferably has a uronic acid content of 0.0 mass % to 4.0 mass %, more preferably 0.0 mass % to 2.0 mass %, even more preferably 0.0 mass % to 2.0 mass %, and still even more preferably 0.0 mass % to 1.0 mass %. It is particularly preferable that the pentosan polysulfate of the present invention has a uronic acid content of substantially 0.0 mass %. The above proportion does not have to be met by a single molecule, but may be satisfied by pentosan polysulfate as an entire mixture of individual molecules.

That is, the pentosan polysulfate of the present invention preferably has a structure represented by Formula I.

Formula I

In Formula I, each R independently represents a hydrogen atom, —COCH$_3$, or —SO$_3$X, and at least one R per molecule is —SO$_3$X, wherein X represents a hydrogen atom or a monovalent or divalent; and n represents an integer of 1 or more and 30 or less.

The compound represented by Formula I is preferably a compound represented by the following Formula I$^X$. That is, it is preferable that the terminal R is not —COCH$_3$.

Formula I$^X$

In Formula I$^X$, R$^X$ each independently represents a hydrogen atom or —SO$_3$X.

In the pentosan polysulfate of the present invention, it is preferable that 50% or more, more preferably 70% or more, and even more preferably 90% or more, of the total number of Rs in Formula II are —SO$_3$X; and that 8% or less, more preferably 4% or less, and even more preferably 1% or less, of the total number of Rs in Formula II are —COCH$_3$. It is particularly preferable that none of the Rs are —COCH$_3$. More specifically, it is particularly preferable that each R independently represents a hydrogen atom or —SO$_3$X. In other words, the pentosan polysulfate of the present invention preferably contains no acetyl groups.

The above proportion does not have to be met by a single molecule, but may be satisfied by pentosan polysulfate as an entire mixture of individual molecules.

X is preferably a hydrogen atom, sodium, potassium, or calcium. It is more preferably sodium, potassium, or calcium, and even more preferably sodium.

n is preferably 3 or more, more preferably 4 or more, and even more preferably 5 or more. On the other hand, n is preferably 30 or less, more preferably 25 or less, and even more preferably 20 or less.

The pentosan polysulfate of the present invention may be a mixture of molecules represented by Formula I that are different from each other in the n value, the kind of substituent R, and/or the degree of substitution.

Pentosan polysulfate has a structure obtained by sulfation of xylooligosaccharides. Among xylooligosaccharides, neutral xylooligosaccharides are xylooligosaccharides that do not contain uronic acid. Acidic xylooligosaccharides are xylooligosaccharides in which at least one uronic acid is bound to at least one of the xylose units in a xylooligosaccharide molecule. That is, acidic xylooligosaccharides have at least one uronic acid residue as a side chain per xylooligosaccharide molecule. The average number of uronic acid residues per acidic xylooligosaccharide molecule is preferably 1 or more and 3 or less, more preferably 1 or more and 2 or less. The number of uronic acid residues contained per xylooligosaccharide molecule can be measured by the carbazole-sulfuric acid method, or the colorimetric method using sodium tetraborate.

The sulfur content of the pentosan polysulfate of the present invention is preferably 10.0 mass % or more, more preferably 12.0 mass % or more, even more preferably 15.5 mass % or more, and particularly preferably 16.5 mass % or more. The sulfur content of the pentosan polysulfate is preferably 20.0 mass % or less. Here, the sulfur content of pentosan polysulfate is a value determined according to the oxygen flask combustion method described in the Japanese Pharmacopoeia.

The pentosan polysulfate of the present invention preferably has an acetyl group content of 0 to 2.0 mass %, more preferably 0 to 1.0 mass %, even more preferably 0 to 0.4 mass %, particularly preferably 0 to 0.3 mass %, and still even more preferably substantially 0 mass %. When the acetyl group content of pentosan polysulfate is as described above, higher anti-Xa activity can be obtained.

The acetyl group content of polysulfate pentosan can be calculated from the integral ratio of peaks in 1H-NMR measurement. Specifically, first, $^1$H-NMR measurement is performed using a $^1$H-NMR measurement solution containing a specific amount of pentosan polysulfate and a specific amount of an internal standard substance. By comparing the peak for acetyl group to the peak for a specific group of the internal standard substance in the obtained spectrum to obtain an integral ratio thereof, the molar amount of acetyl groups in the solution is obtained. The molar amount of acetyl groups is then multiplied by 43; and the obtained value is divided by the average molecular weight obtained separately, so as to obtain the mass % of acetyl groups.

The weight average molecular weight (Mw) of the pentosan polysulfate of the present invention is not particularly limited; and may be, for example, 4000 or less, 3900 or less, or 3800 or less. In this case, the lower limit of the weight average molecular weight (Mw) of the pentosan polysulfate is preferably 1000.

The weight average molecular weight (Mw) of the pentosan polysulfate may be greater than 4000, 5000 or more, 7000 or more, 10000 or more, 15000 or more, or 20000 or more.

The number average molecular weight (Mn) of the pentosan polysulfate is not particularly limited; and may be, for example, 4000 or less, 3900 or less, 3800 or less, or 3750 or less. In this case, the lower limit of the number average molecular weight (Mn) of the pentosan polysulfate is preferably 300.

The number average molecular weight (Mn) of the pentosan polysulfate may be 5000 or more, 7000 or more, 10000 or more, 15000 or more, or 20000 or more.

The weight average molecular weight (Mw) and the number average molecular weight (Mn) of the pentosan polysulfate of the present invention can be measured by GPC (gel permeation chromatography). As the GPC column, a YMC-Pack Diol-300 and YMC-Pack Diol-60 (both manufactured by YMC) connected to each other can be used. The GPC conditions can be, for example, the following conditions.

Eluent: 25 mM potassium dihydrogen phosphate/25 mM dipotassium hydrogen phosphate/50 mM potassium chloride
Flow rate: 0.7 mL/min
Measurement temperature: 40° C.
Detector: refractive index detector The dispersion degree of the pentosan polysulfate is preferably 1.00 or more and 1.6 or less, more preferably 1.00 or more and 1.5 or less. The dispersion degree of the pentosan polysulfate is also preferably 1.00 or more and 1.4 or more. The degree of dispersion (D) of the pentosan polysulfate is calculated by the following formula.

Degree of dispersion ($D$)=Weight average molecular weight (Mw)/Number average molecular weight (Mn)

The pentosan polysulfate obtained by the production method of the present invention described below has high purity, and tends to have a narrow molecular weight distribution. The pentosan polysulfate obtained by the production method of the present invention has excellent quality stability.

Applications of Pentosan Polysulfate: Pharmaceutical Composition and Anticoagulant The pentosan polysulfate of the present invention can be used for applications, such as pharmaceuticals, foods, and cosmetics. For example, a pharmaceutical composition comprising, as an active ingredient, the pentosan polysulfate of the present invention (pentosan polysulfate, a pharmaceutically acceptable salt thereof, or a solvate thereof) can be provided. In particular, since the pentosan polysulfate has an anticoagulant activity, the above-described pharmaceutical composition can be used as an anticoagulant.

In general, anticoagulant activity is based on the activity of inhibiting blood coagulation factors. Specifically, when anticoagulant activity is high, a blood coagulation reaction is inhibited. Blood coagulation factors mean the action system of a series of molecules in a living body for coagulating blood when bleeding etc. Many blood coagulation factors are successively activated to thereby agglutinate fibrin, and stop bleeding in the bleeding area. Representative examples of blood coagulation factors include factor Xa and factor IIa. Blood coagulation can be inhibited by inhibiting the activity of these factors.

The factor Xa inhibitory activity (anti-Xa activity) of pentosan polysulfate is preferably 0.10 IU/mg or more, and more preferably 0.12 IU/mg or more.

The factor IIa inhibitory activity (anti-IIa activity) of pentosan polysulfate is preferably 0.50 IU/mg or less, more preferably 0.40 IU/mg or less, and further preferably 0.30 IU/mg or less.

Here, the factor Xa inhibitory activity (anti-Xa activity) can be measured using Test Team (registered trademark) Heparin S (manufactured by Sekisui Medical Co., Ltd.).

The factor IIa inhibitory activity (anti-IIa activity) can be measured using Biophen heparin anti-IIa (manufactured by Hyphen BioMed).

The activity ratio of the factor Xa inhibitory activity (anti-Xa activity) of pentosan polysulfate to the factor IIa inhibitory activity (anti-IIa activity) of the pentosan polysulfate is preferably within a predetermined range. Specifically, the anti-Xa activity/anti-IIa activity ratio is preferably 0.50 or more, more preferably 1.00 or more, even more preferably 1.10 or more, and still even more preferably 1.20 or more.

The pentosan polysulfate of the present invention can have anti-Xa activity, anti-IIa activity, and an anti-Xa activity/anti-IIa activity ratio that are controlled within the above-described ranges. In particular, the pentosan polysulfate of the present invention can have anti-IIa activity suppressed lower than anti-Xa activity. When the anti-Xa activity/anti-IIa activity ratio is controlled to fall within the above-mentioned range, the anticoagulant activity can be more effectively increased; and the occurrence of side effects, such as an increased risk of bleeding or a decrease of platelets, can be suppressed.

A pharmaceutical composition comprising the pentosan polysulfate of the present invention can be used, for example, as a surface treatment agent for medical devices or medical materials. The pharmaceutical composition can be used, for example, as a surface treatment agent for implantable artificial organs, artificial blood vessels, catheters, stents, blood bags, contact lenses, intraocular lenses, and surgical auxiliary instruments. Examples of methods for immobilizing the pharmaceutical composition on the surface of a medical device or a medical material include a method comprising bringing the pharmaceutical composition into contact with the medical device or the medical material, and irradiating the contact portion with radiation.

The pharmaceutical composition may have any dosage form, and can be formed into, for example, an oral administration preparation, an injection, or an external preparation.

Method for Producing Pentosan Polysulfate

The pentosan polysulfate of the present invention can be produced by sulfating a neutral xylooligosaccharide. The pentosan polysulfate of the present invention is preferably produced by sulfating a neutral xylooligosaccharide. The neutral xylooligosaccharide can be obtained by extraction from a plant-derived raw material, optionally followed by depolymerization, or by polymerizing D-xylose.

Figure 1:
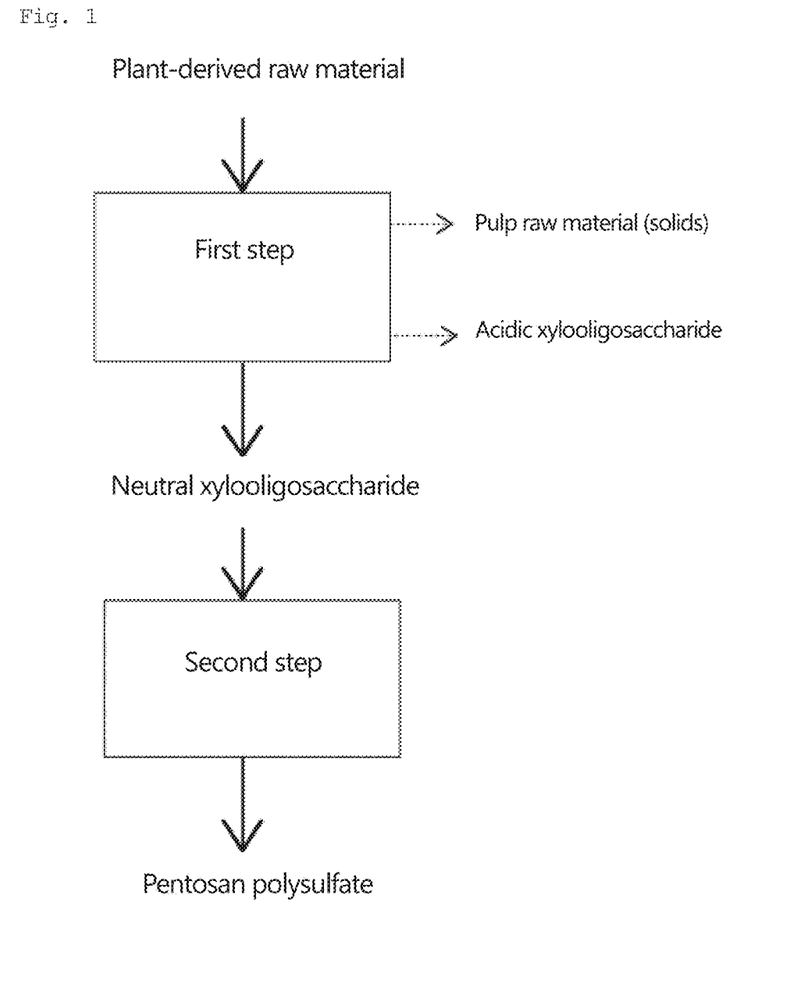
FIG. 1 is a diagram illustrating a method for producing pentosan polysulfate.

The pentosan polysulfate of the present invention can be obtained, for example, by a method for producing pentosan polysulfate, the method comprising a first step of obtaining a neutral xylooligosaccharide from a plant-derived raw material and a second step of obtaining pentosan polysulfate from the neutral xylooligosaccharide, as shown in FIG. 1. In this method, the first step includes a step of depolymerizing a plant-derived raw material. Since the method comprises the step of depolymerizing a plant-derived raw material and the sulfation step in this order, the method can efficiently produce pentosan polysulfate. The method for producing pentosan polysulfate may further include a deacetylation step. By including a deacetylation step, the method can produce a pentosan polysulfate having a low acetyl group content.

Plant-Derived Raw Material

Neutral xylooligosaccharides can be obtained by depolymerizing plant-derived raw materials. Examples of plant-derived raw materials include wood-derived raw materials, seed-derived raw materials, grain-derived raw materials, fruit-derived raw materials, and the like. Further, examples of plant-derived raw materials that can be used include cottons such as cotton linter and cotton lint; herbaceous plants such as kenaf, hemp, ramie, and rice straw; and the like. As the plant-derived raw material, the above-mentioned raw materials derived from various sources may also be used in combination.

Among these, wood-derived raw materials are preferably used as the plant-derived raw material. Examples of usable wood-derived raw materials include wood raw materials such as softwoods and hardwoods. The wood-derived raw material is preferably at least one selected from softwoods and hardwoods; and hardwoods are more preferably used. The wood-derived raw material may be a mixture of softwood and hardwood. A bark may also be used as the wood-derived raw material.

Examples of hardwoods include beech, *Eucalyptus globulus, Eucalyptus grandis, Eucalyptus urograndis, Eucalyptus pellita, Eucalyptus braciana, Acacia mearnsii*, and the like. Examples of softwoods include Japanese cedar, Japanese cypress, pine, hiba, Japanese hemlock, and the like.

The wood-derived raw material preferably has a specific gravity of 450 kg/m³ or more and 700 kg/m³ or less, and more preferably 500 kg/m³ or more and 650 kg/m³ or less. When the wood-derived raw material has a specific gravity within the above-described range, the efficiency of producing neutral xylooligosaccharide can be further enhanced.

The wood-derived raw material is preferably wood chips obtained by crushing one or more of the above-mentioned woods. When wood chips are used as a plant-derived raw material, the depolymerization of a plant-derived raw material can be efficiently performed, and the efficiency of producing neutral xylooligosaccharide can be enhanced.

First Step

Depolymerization Step

The first step includes a step of depolymerizing a plant-derived raw material. In the step of depolymerizing a plant-derived raw material, the plant-derived raw material is chemically and/or physically decomposed to produce a neutral xylooligosaccharide. Examples of the chemical and/or physical decomposition step include a heat treatment step, an alkali treatment step, an acid treatment step, an enzyme treatment step, an ionic liquid treatment step, a catalytic treatment step, and the like. Among these steps, the depolymerization step is preferably a heat treatment step or an enzyme treatment step; and is more preferably a heat treatment step. The heat treatment step may be a heating and pressurizing step.

The depolymerization step is preferably performed under non-alkaline conditions (at pH 9 or less, and preferably pH 8 or less).

The heat treatment step is a step of heating a plant-derived raw material in the presence of a solution. Since the plant-derived raw material is hydrolyzed in such a heat treatment step, the heat treatment step is sometimes referred to as a hydrolysis treatment step or a pre-hydrolysis treatment step. The solution used in the heat treatment step is preferably water. The ratio (mass ratio) of water to the plant-derived raw material is preferably in the range of 1:1 to 1:10. When the ratio of water to the plant-derived raw material is set within the above-described range, the hydrolysis reaction can be efficiently performed. The water used in the heat treatment step may be water added separately from the plant-derived raw material; or a part of the water may be water originally contained in the plant-derived raw material.

In the heat treatment step, other chemicals may also be added, in addition to the plant-derived raw material and water. Examples of such other chemicals include alkalis, acids, and chelating agents. Further, chemicals that directly or indirectly assist the depolymerization of polysaccharides, such as scale inhibitors, pitch control agents, and ionic liquids, may also be added.

The heat treatment step is a step of heating a plant-derived raw material in the presence of water. The heating temperature (liquid temperature) in this step is preferably 30° C. or higher, more preferably 50° C. or higher, even more preferably 75° C. or higher, still even more preferably 90° C. or higher, particularly preferably 100° C. or higher, and most preferably 120° C. or higher. On the other hand, the heating temperature (liquid temperature) is preferably 300° C. or lower, more preferably 250° C. or lower, and even more preferably 200° C. or lower.

The treatment time in the heat treatment step can be determined, as appropriate, according to the treatment temperature. The treatment time is, for example, preferably 5 minutes or more, more preferably 10 minutes or more, and even more preferably 20 minutes or more. The P factor expressed by the following formula is a product of the heat treatment temperature and the heat treatment time. It is preferable to adjust the P factor within a preferred range.

$$P = \int_{t_0}^{t} \frac{k_{H1(T)}}{k_{100°\ C.}} \cdot dt = \int_{t_0}^{t} \text{Exp} \cdot \left(40.48 - \frac{15106}{T}\right) \cdot dt$$

In the above formula, P represents a P factor, T represents an absolute temperature (° C.±273.5), t represents the heat treatment time, and $K_{H1(T)}/K_{100°\ C.}$ represents the relative rate of hydrolysis of glycosidic bonds.

In the heat treatment step, the P factor is preferably set at 200 or more, more preferably 250 or more, and even more preferably 300 or more. On the other hand, the P factor is preferably 1000 or less. In the heat treatment step, the P factor is adjusted as appropriate so that the average degree of polymerization and the molecular weight of neutral xylooligosaccharide can be within desired ranges, whereby the molecular weight of the obtained pentosan polysulfate can be adjusted.

In the heat treatment step, the solution containing a plant-derived raw material preferably has a pH of 9 or less, more preferably pH 8 or less, and even more preferably pH 7 or less. That is, the heat treatment step is preferably performed under non-alkaline conditions. The pH values described above refer to the pH of the solution before the heat treatment.

In the heat treatment step, a raw material-derived acid may be dissociated, and acid hydrolysis may proceed at least partially. Examples of plant raw material-derived acids include organic acids, such as acetic acid and formic acid. In this case, the pH of the solution containing a plant-derived raw material is further decreased after the acid hydrolysis.

The method for producing pentosan polysulfate preferably comprises a heat treatment step as the first step. This can enhance the efficiency of producing neutral xylooligosaccharide, and further enhance the efficiency of producing pentosan polysulfate. When the method includes a heat treatment step as the first step, the number of steps required to produce neutral xylooligosaccharide can be significantly reduced, as compared with the conventional methods. By including a heat treatment under non-alkaline conditions as the first step, the method can efficiently produce neutral xylooligosaccharide with suppressed coloration, because the neutral xylooligosaccharide is not substituted with hexenuronic acid.

The depolymerization step is preferably a heat treatment step; however, it may be a step other than the heat treatment step. For example, when the depolymerization step is an enzyme treatment step, the depolymerization step includes a step of mixing a plant-derived raw material with an enzyme. Examples of usable enzymes include hemicellulase and the like. Specific examples include commercially available enzyme preparations, such as Cellulosin HC100 (trade name, manufactured by HBI Enzymes Inc.), Cellulosin TP25 (trade name, manufactured by HBI Enzymes Inc.), Cellulosin HC (trade name, manufactured by HBI Enzymes Inc.), Cartazyme (trade name, manufactured by Clariant AG), Ecopulp (trade name, manufactured by Rohm Enzyme GmbH), Sumizyme (trade name, manufactured by Shin Nihon Chemicals Corporation), Pulpzyme (manufactured by Novo Nordisk), and Multifect 720 (Genencor); and xylanase produced by microorganisms belonging to genus *Trichoderma*, genus *Thermomyces*, genus *Aureobasidium*, genus *Streptomyces*, genus *Aspergillus*, genus *Clostridium*, genus *Bacillus*, genus *Thermotoga*, genus *Thermoascus*, genus *Cardoceram*, genus *Thermomonospora*, or the like.

In the enzyme treatment step, an enzyme is added to a solution prepared by mixing a plant-derived raw material with water. The temperature of the solution during this treatment is preferably 10° C. or higher and 90° C. or lower, and more preferably 30° C. or higher and 60° C. or lower. The temperature of the solution is preferably a temperature close to the optimal temperature of the enzyme used. The pH of the solution is also preferably adjusted to a range in which the activity of the enzyme is enhanced. For example, the pH of the solution is preferably adjusted to a pH of 3 or more and a pH of 10 or less.

When the depolymerization step is an alkali treatment step or an acid treatment step, the depolymerization step comprises a step of mixing a plant-derived raw material with an alkaline solution or an acid solution. In the alkali treatment step, sodium hydroxide or potassium hydroxide is preferably added. In the acid treatment step, hydrochloric acid, sulfuric acid, acetic acid, or the like is preferably added. In such cases as well, heating or pressurization may be carried out, as appropriate.

When the depolymerization step is at least one selected from an enzyme treatment step, an alkali treatment step, and an acid treatment step, the production method may further comprise, after the treatment step, a squeezing step, an extraction step, a heating step, a filtration step, a separation step, a purification step, a concentration step, a desalination step, or the like. The method may further comprise a molecular weight reducing step performed after the treatment step. Examples of other steps include the steps described in JP2003-183303A, the contents of which are incorporated herein by reference.

Filtration Step

The first step may further comprise a filtration step performed after the depolymerization step described above. In the filtration step, the reaction mixture is separated into solids of the plant-derived raw material, and a solution other than the solids. More specifically, when the first step includes a filtration step performed after the depolymerization step, the reaction product is separated into solids, which are used as a pulp raw material, and a filtrate. The solids used as a pulp raw material are subjected to a digestion step or the like as a post-step, to provide a cellulose raw material (dissolving pulp).

The recovered filtrate can be separated into a gas layer and a liquid layer. Since the gas layer contains a large amount of furfurals, furfurals can be isolated by collecting these furfurals from the gas layer. On the other hand, the liquid layer contains a large amount of hemicellulose including neutral xylooligosaccharide and acidic xylooligosaccharide. In the step described below, the neutral xylooligosaccharide contained in this liquid layer can be separated and purified.

Separation and Purification Step

The first step may further comprise a separation and purification step performed after the depolymerization step. When the first step comprises the filtration step described above, a separation and purification step is preferably provided after the filtration step.

Figure 2:
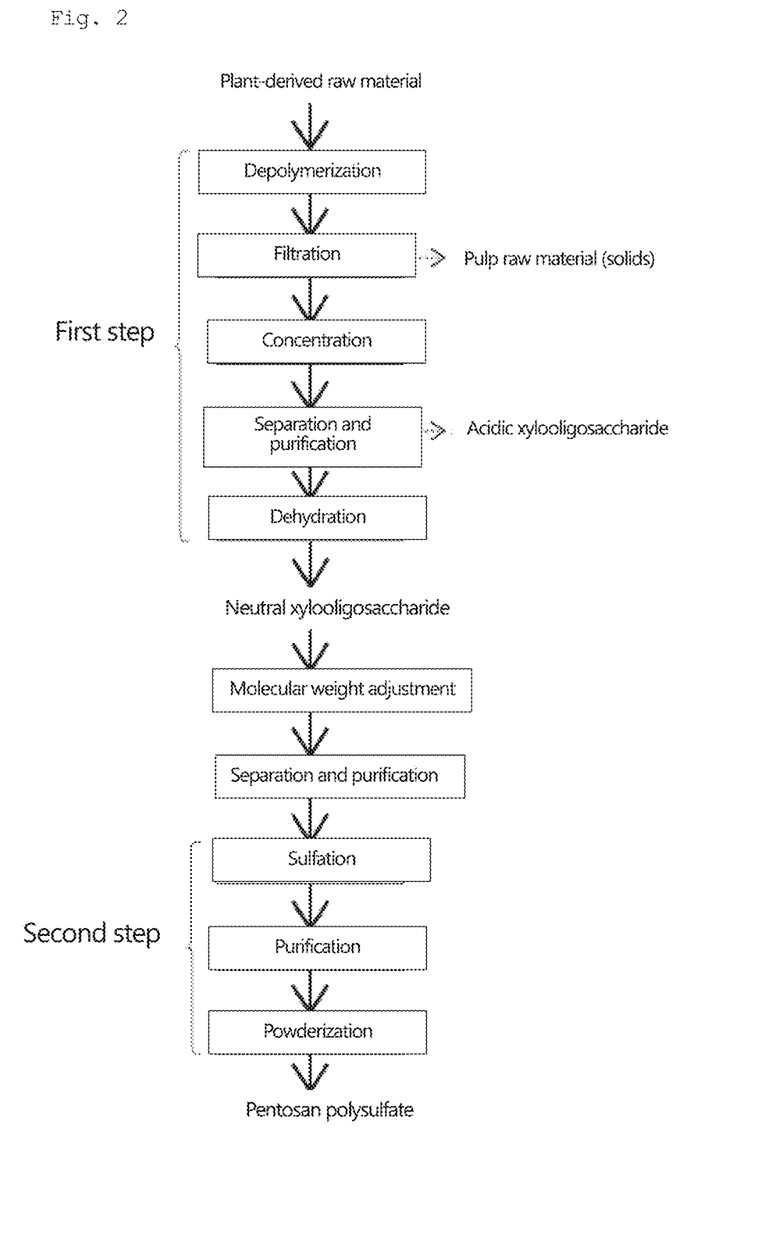
FIG. 2 is a diagram illustrating a method for producing pentosan polysulfate.

FIG. 2 is a flow chart in which a filtration step is provided after the depolymerization step, and a separation and purification step is provided after the filtration step. The first step may include a separation and purification step immediately after the depolymerization step. However, the first step preferably includes a filtration step performed after the depolymerization step; and includes a step of separating neutral xylooligosaccharide from the obtained filtrate, and purifying the neutral xylooligosaccharide. The filtration step may be provided as a part of the separation and purification step; or may be provided as one step that is independent from the separation and purification step, as shown in FIG. 2. The separation and purification step is a step of separating and purifying neutral xylooligosaccharide. Since the filtrate obtained in the filtration step contains various saccharides, such as acidic xylooligosaccharide, in addition to neutral xylooligosaccharide, the separation and purification step is also a step of removing such xylooligosaccharides other than neutral xylooligosaccharide.

In the separation and purification step, for example, ion exchange chromatography, affinity chromatography, gel filtration, ion exchange treatment, NF membrane treatment, UF membrane treatment, RO membrane treatment, activated carbon treatment, or like methods are preferably used. In the separation and purification step, it is also preferable to perform the above methods in combination. In particular, when ion exchange chromatography is performed in the separation and purification, neutral xylooligosaccharide can be selectively separated and purified. In ion exchange chromatography, acidic xylooligosaccharide is adsorbed; accordingly, neutral xylooligosaccharide can be mainly obtained from the permeate. More specifically, sugar liquid is first treated with a strong cation exchange resin to remove metal ions from the sugar liquid. Subsequently, using a strong anion exchange resin, sulfate ions or the like are removed from the sugar liquid. The resulting sugar liquid is treated with a weak anion exchange resin to adsorb acidic xylooligosaccharide on the resin.

Concentration Step

The first step may further comprise a concentration step. The concentration step is preferably provided, for example, after the filtration step and before the separation and purification step, as shown in FIG. 2. When the first step includes such a concentration step, the separation and purification step can be more efficiently performed, thus increasing the efficiency of producing pentosan polysulfate.

Examples of the concentration step include a membrane treatment step using an NF membrane, an ultrafiltration membrane, a reverse osmosis membrane, or the like; a concentration step using evaporation etc.; and the like.

In the concentration step, the solution is preferably concentrated, so that the neutral xylooligosaccharide content is 10% or more and 80% or less, and more preferably 20% or more and 60% or less, based on the total mass of the concentrate.

Dehydration Step

In the first step, the neutral xylooligosaccharide may be obtained in the form of a neutral xylooligosaccharide solution; or may be subjected to a dehydration step, and thereby obtained in the form of a neutral xylooligosaccharide concentrate or a neutral xylooligosaccharide powder. When a neutral xylooligosaccharide powder is to be produced, the production method preferably further comprises a powdering step performed after the separation and purification step. When a dehydration step is included in the present invention, sulfation in the sulfation step described below can be performed more efficiently.

In the powdering step, the neutral xylooligosaccharide solution obtained in the separation and purification step is treated, for example, using a spray dryer, a freeze-drying machine, a hot-air drying machine, or a water-soluble organic solvent, to thereby obtain a neutral xylooligosaccharide powder.

Second Step

Sulfation Step

The neutral xylooligosaccharide obtained in the first step is sulfated in a second step to thereby obtain pentosan polysulfate. That is, the second step comprises a sulfation step. The average degree of polymerization of the neutral xylooligosaccharide to be subjected to sulfation is preferably adjusted, as appropriate, according to the molecular weight of pentosan polysulfate to be obtained as a final product.

The average degree of polymerization of the neutral xylooligosaccharides can be calculated by dividing the total sugar amount of the neutral xylooligosaccharide by the amount of reducing sugar. In calculation of the total sugar amount, first, an acidic xylooligosaccharide solution is maintained at 50° C. and centrifuged at 15000 rpm for 15 minutes. Thereafter, the total sugar amount of the supernatant is quantified by the phenol-sulfuric acid method ("*Kangento no Teiryo-Ho* (Method of Quantifying Reducing Sugar)"; published by Gakkai Shuppan Center). The calibration curve to be used in the quantification is produced using D-xylose (Wako Pure Chemical Industries, Ltd.). The amount of reducing sugar is quantified by the Somogyi-Nelson method ("*Kangento no Teiryo-Ho* (Method of Quantifying Reducing Sugar)"; published by Gakkai Shuppan Center). The calibration curve to be used in this quantification is also produced using D-xylose (Wako Pure Chemical Industries, Ltd.).

In the sulfation step, sulfuric acid or a sulfuric acid derivative is added to the neutral xylooligosaccharide solution to sulfate neutral xylooligosaccharide. Examples of sulfuric acid derivatives include sulfur trioxide pyridine complex, chlorosulfonic acid, and the like. In this step, the concentration of the neutral xylooligosaccharide solution is preferably 0.1 mass % or more and 20 mass % or less, and sulfuric acid is preferably added to the neutral xylooligosaccharide solution having such a concentration in an amount of 0.1 mass % or more and 50 mass % or less. The neutral xylooligosaccharide solution after addition of sulfuric acid preferably has a pH of 7 or more.

Post-Sulfation Purification Step

The second step may further comprise a post-sulfation purification step performed after the sulfation. When the second step includes such a post-sulfation purification step, a high-purity pentosan polysulfate can be obtained.

In the post-sulfation purification step, for example, centrifugation, membrane filtration, dialysis, water-soluble organic solvent treatment, activated carbon treatment, or like method is preferably used. Among these, water-soluble organic solvent treatment and activated carbon treatment are preferably used, because sulfonated pentosan polysulfate can be selectively separated and purified.

Powdering Step

In the second step, sulfated pentosan polysulfate may be obtained in the form of a pentosan polysulfate solution; or may be subjected to a powdering step, and thereby obtained in the form of a pentosan polysulfate powder. When a pentosan polysulfate powder is to be produced, the second step preferably further includes a powdering step performed after the post-sulfation purification step.

In the powdering step, the pentosan polysulfate solution obtained in the post-sulfation purification step can be treated, for example, using a spray dryer, a freeze-drying machine, a hot-air drying machine, a water-soluble organic solvent, or the like, to thereby obtain a pentosan polysulfate powder.

Pentosan polysulfate is obtained by performing the second step described above. The pentosan polysulfate thus obtained preferably has a sulfur content of 10 mass % or more to 20 mass % or less, based on the total mass of the pentosan polysulfate. The sulfur content of pentosan polysulfate can be measured by the oxygen flask combustion method of the General Tests of the Japanese Pharmacopoeia.

Deacetylation Step

In the production of pentosan polysulfate, deacetylation may be performed. The deacetylation step is preferably performed at any stage after the depolymerization step. The deacetylation step can reduce the acetyl group content of pentosan polysulfate. Specifically, the deacetylation step is a step of adding a base to a solution containing a substance obtained from a plant-derived raw material, such as neutral xylooligosaccharide (also herein referred to as a "solution containing neutral xylooligosaccharide or the like"), so as to adjust the solution to pH 11 or more. In the deacetylation step, the solution obtained after the depolymerization, the filtrate obtained by the filtration step, the solution containing neutral xylooligosaccharide after the separation and purification step and before the sulfation step, the solution containing neutral xylooligosaccharide after the sulfation step (pentosan polysulfate), or the like may be adjusted to a pH of 11 or more. Among these solutions, when the solution containing neutral xylooligosaccharide after the separation and purification step and before the sulfation step is adjusted to pH 11 or more, a pentosan polysulfate having stable quality and a reduced acetyl group content can be obtained, and the sites where acetyl groups were bound can also be sulfated. Therefore, the sulfation efficiency, and thus the efficiency of producing pentosan polysulfate, can be increased. When the solution containing xylooligosaccharide obtained after the sulfation step (pentosan polysulfate) is adjusted to pH 11 or more, the purification step can be performed more efficiently. The solution containing neutral xylooligosaccharide or the like is preferably an aqueous solution. The solution containing neutral xylooligosaccharide may also be referred to herein as the neutral xylooligosaccharide solution.

The pH applied in the deacetylation step is preferably pH 11 to 14, and more preferably pH 12 to 13. The solution to be subjected to the deacetylation step is preferably maintained at pH 11 or more for 0.5 hours or more, more preferably at pH 11 or more for 1.0 hour or more, even more preferably at pH 11 or more for 2.0 hours or more, and particularly preferably at pH 11 or more for 3.0 hours or more. In particular, when the pH is less than 12, the solution is preferably maintained for 1.0 hour or more. Particularly preferred conditions may be, for example, conditions in which the solution is maintained at pH 12 to 13 for 3 hours or more.

While the solution is maintained in the above-described pH range, the solution is preferably stirred. The temperature applied while the solution is maintained in the above-described pH range is not particularly limited, but is preferably room temperature.

In the deacetylation step, a base may be added to a solution to be subjected to the deacetylation step (a solution containing neutral xylooligosaccharide or the like). The base to be added is not particularly limited, as long as the desired pH can be achieved. The base is preferably sodium hydroxide.

The deacetylation step may comprise a pH adjustment step of adjusting, to less than pH 11, the pH of a solution that has a pH of 11 or more, which results from the addition of a base after being maintained at the above-described pH. In the pH adjustment step, the solution may be adjusted to, for example, pH 9 or less, pH 8 or less, pH 7 or less, pH 6 or less, pH 5 or less, or pH 4 or less. The adjustment may be performed by adding an acid. Examples of usable acids include hydrochloric acid.

The deacetylation step preferably comprises a desalting step performed after the pH adjustment step. Desalting can be performed, for example, using a dialysis membrane or an NF membrane.

The deacetylation step may further comprise a step of powdering the obtained product for the subsequent treatment.

Other Steps

Molecular Weight Adjustment Step

The method for producing pentosane polysulfate may further comprise a molecular weight adjustment step between the first step and the second step. When the method for producing pentosan polysulfate includes a deacetylation step, the molecular weight adjustment step may be performed before or after the deacetylation step. FIG. 2 is a flow diagram including a molecular weight adjustment step between the first step and the second step. As shown in FIG. 2, in the molecular weight adjustment step, the molecular weight of the neutral xylooligosaccharide obtained in the first step is adjusted. For example, in the molecular weight adjustment step, the molecular weight of the neutral xylooligosaccharide can be reduced.

In the molecular weight adjustment step, a pentosan polysulfate having a weight average molecular weight of 1000 or more and 30000 or less can be obtained by performing, for example, acid treatment, alkali treatment, enzyme treatment, NF membrane treatment, UF membrane treatment, RO membrane treatment, gel filtration treatment, activated carbon treatment, ion exchange treatment, electrodialysis treatment, or the like. It is also possible to use a method of selectively collecting pentosan polysulfate having a desired weight average molecular weight by performing a membrane treatment or the like in the molecular weight adjustment step.

Post-Molecular-Weight-Adjustment Separation and Purification Step

The method for producing pentosan polysulfate may further comprise a post-molecular-weight-adjustment separation and purification step performed after the molecular weight adjustment step. Examples of the post-molecular-weight-adjustment separation and purification step may include gel filtration, ion exchange treatment, NF membrane treatment, UF membrane treatment, RO membrane treatment, electrodialysis treatment, activated carbon treatment, water-soluble organic solvent treatment, chromatographic treatment, and the like. When the production method includes such a post-molecular-weight-adjustment separation and purification step, neutral xylooligosaccharide having a desired molecular weight obtained in the molecular weight adjustment step can be selectively collected, and pentosan polysulfate having a narrow molecular weight distribution can be efficiently obtained.

EXAMPLES

The features of the present invention are described below more specifically with reference to Production Examples. The materials, amounts used, proportions, treatment content, treatment procedures, and the like described in the following Production Examples can be appropriately changed to the extent that such changes do not depart from the spirit of the present invention. Accordingly, the scope of the present invention should not be construed as being limited by the following specific examples.

Production of Neutral Xylooligosaccharide

Forty parts by mass of water was added to 10 parts by mass of wood chips (hardwood), and a heat treatment was performed at 160° C. for 3 hours. The resulting mixture was then subjected to solid-liquid separation using a Screw Press (manufactured by Shinryo Seisakusho: 250×1000 SPH-EN), and the filtrate was recovered. The filtrate was filtered through a bag filter with a micron rate of 1 μm (manufactured by ISP Filters). After 5 parts by mass of activated carbon (PM-SX; manufactured by Mikura Kasei Kabushiki Kaisha) was added to the obtained filtrate and a treatment was allowed to proceed at 50° C. for 2 hours, the treatment mixture, including the activated carbon, was further filtered through a ceramic filter with a micron rate of 0.2 μm (manufactured by Nihon Pall Co., Ltd.) to recover a clear filtrate. After the clear filtrate was concentrated 20-fold with a reverse osmosis membrane (NTR-7450; manufactured by Nitto Denko Corporation) to obtain a concentrated sugar liquid, the concentrated sugar liquid was passed at SV 1.5 through a 4-bed 4-tower type ion exchange resin system consisting of a strong cationic resin (PK-218; manufactured by Mitsubishi Chemical Corporation), a weak anionic resin (WA30; manufactured by Mitsubishi Chemical Corporation), a strong cationic resin (PK-218; manufactured by Mitsubishi Chemical Corporation), and a weak anionic resin (WA30; manufactured by Mitsubishi Chemical Corporation) to thereby recover a neutral xylooligosaccharide solution. Sodium hydroxide was added to the obtained neutral xylooligosaccharide solution to achieve a pH of 13, and the resulting mixture was stirred at room temperature for 3 hours for deacetylation. After hydrochloric acid was added to the obtained solution to achieve a pH of less than 5, and the obtained salt was removed using a dialysis membrane (Spectra/Por 7, CE membrane, MWCO 100-500; manufactured by Spectrum), the resulting mixture was powdered using a freeze-drying machine (manufactured by Eyela).

Production of Acidic Xylooligosaccharide

Forty parts by mass of water was added to 10 parts by mass of wood chips (hardwood), and a heat treatment was performed at 160° C. for 3 hours. The resulting mixture was then subjected to solid-liquid separation using a Screw Press (manufactured by Shinryo Seisakusho: 250×1000 SPH-EN), and the filtrate was recovered. The filtrate was further filtered through a bag filter with a micron rate of 1 µm (manufactured by ISP Filters). After 5 parts by mass of activated carbon (PM-SX; manufactured by Mikura Kasei Kabushiki Kaisha) was added to treat the filtrate at 50° C. for 2 hours, the treatment mixture, including the activated carbon, was further filtered through a ceramic filter with a micron rate of 0.2 µm (manufactured by Nihon Pall Co., Ltd.) to recover a clear filtrate. After the clear filtrate was concentrated 20-fold with a reverse osmosis membrane (NTR-7450; manufactured by Nitto Denko Corporation) to obtain a concentrated sugar liquid, the concentrated sugar liquid was passed at SV 1.5 through a 4-bed 4-tower type ion exchange resin system consisting of a strong cationic resin (PK-218; manufactured by Mitsubishi Chemical Corporation), a weak anionic resin (WA30; manufactured by Mitsubishi Chemical Corporation), a strong cationic resin (PK-218; manufactured by Mitsubishi Chemical Corporation), and a weak anionic resin (WA30; manufactured by Mitsubishi Chemical Corporation). Acidic xylooligosaccharide was adsorbed on the weak anionic resin of the second and fourth towers. A 50 mM sodium chloride aqueous solution was then passed through the second and fourth towers at SV 1.5 to recover an acidic xylooligosaccharide solution. Sodium hydroxide was added to the obtained acidic xylooligosaccharide solution to achieve a pH of 13, and the resulting mixture was stirred at room temperature for 3 hours for deacetylation. After hydrochloric acid was added to the resulting solution to achieve a pH of less than 5 and desalting was performed using a dialysis membrane (Spectra/Por 7, CE membrane, MWCO 100-500; manufactured by Spectrum), the resulting mixture was powdered using a freeze-drying machine (manufactured by Eyela).

Production of Pentosan Polysulfate Sodium

Example 1

25 mL of N,N-dimethylformamide, 12.4 g of sulfur trioxide pyridine complex, and 1.5 g of neutral xylooligosaccharide powder produced by the method described above were placed in a 100-mL separable flask, and a reaction was allowed to proceed at 40° C. for 3 hours. After cooling, the obtained reaction mixture was added dropwise to 500 mL of ethanol. The generated precipitate was collected by filtration, and 30 mL of water was added to dissolve the precipitate therein. A sodium hydroxide solution was added to the obtained solution to achieve a pH of 10. The resulting solution was added dropwise to 500 mL of ethanol, and the obtained precipitate was then collected by filtration. Thereafter, 30 mL of water was added to dissolve the precipitate therein; and activated carbon was added to the solution and stirred, followed by filtration. The filtrate was concentrated using an evaporator, and powdered using a freeze-drying machine (manufactured by Eyela).

Example 2

Pentosan polysulfate sodium was obtained in the same manner as in Example 1, except that a mixture of 1.125 g of neutral xylooligosaccharide powder and 0.375 g of acidic xylooligosaccharide was used in place of 1.5 g of the neutral xylooligosaccharide powder of Example 1.

Example 3

Pentosan polysulfate sodium was obtained in the same manner as in Example 1, except that a mixture of 0.75 g of neutral xylooligosaccharide powder and 0.75 g of acidic xylooligosaccharide was used in place of 1.5 g of the neutral xylooligosaccharide powder of Example 1.

Comparative Example 1

Pentosan polysulfate sodium was obtained in the same manner as in Example 1, except that a mixture of 0.375 g of neutral xylooligosaccharide powder and 1.125 g of acidic xylooligosaccharide was used in place of 1.5 g of the neutral xylooligosaccharide powder of Example 1.

Comparative Example 2

Pentosan polysulfate sodium was obtained in the same manner as in Example 1, except that acidic xylooligosaccharide powder was used in place of the neutral xylooligosaccharide powder of Example 1.

Uronic Acid Content

About 10 mg of pentosan polysulfate sodium obtained in each of the Examples was weighed out and dissolved in distilled water to make the volume exactly 25 mL. 1 mL of each solution was placed in a test tube. While the solution was cooled in ice water, 5 mL of a solution of 0.025M sodium tetraborate in sulfuric acid was added and mixed, and the resulting mixture was heated in a water bath for 10 minutes. Immediately after heating, the resulting mixture was ice-cooled, and 0.2 mL of a carbazole reagent was added and mixed. The resulting mixture was heated in a water bath for 15 minutes, and then allowed to cool to obtain a sample solution. Separately, glucuronic acid standard stock solutions in a concentration of 10 to 100 µg/mL were prepared and subjected to the same procedure as above to obtain standard solutions. 1 mL of distilled water was also subjected to the same procedure, and the resulting liquid was used as a control. Absorbance at a wavelength of 530 nm was measured. Calibration curves were prepared from the absorbance of the standard solutions, and the amount of glucuronic acid (µg) was determined. The uronic acid content (mass %) was calculated according to the following formula. When the quantitative value was negative, it was regarded as 0%.

Uronic acid content (mass %)=Amount of glucuronic acid (µg)/(Weighed amount of pentosan polysulfate sodium (mg)×$\frac{1}{25}$)/10

Sulfur Content

The sulfur content was measured by the oxygen flask combustion method described in the Japanese Pharmacopoeia.

Average Molecular Weight

The weight average molecular weight (Mw) of pentosan polysulfate was measured by GPC (gel permeation chromatography). A YMC-Pack Diol-300 and YMC-Pack Diol-60 (both manufactured by YMC) connected to each other can be used as a GPC column. GPC was performed under the following conditions.

Eluent: 25 mM potassium dihydrogen phosphate/25 mM dipotassium hydrogen phosphate/50 mM potassium chloride
Flow rate: 0.7 mL/min
Measurement temperature: 40° C.
Detector: refractive index detector

TABLE 1

|  | Comparative Example 2 | Comparative Example 1 | Example 3 | Example 2 | Example 1 |
|---|---|---|---|---|---|
| Weight average molecular weight | 2781 | 2487 | 2387 | 2168 | 2053 |
| Uronic acid content (mass %) | 12.61 | 7.94 | 5.67 | 1.64 | 0.00 |
| Sulfur content (mass %) | 13.28 | 14.33 | 15.12 | 15.09 | 15.34 |
| Anti-II activity (IU/mg) | 0.3361 | 0.2398 | 0.1722 | 0.1254 | 0.0301 |
| Anti-Xa activity (IU/mq) | 0.2246 | 0.2260 | 0.2563 | 0.2579 | 0.2381 |
| Anti-Xa/anti-II activity ratio | 0.668 | 0.942 | 1.488 | 2.056 | 7.910 |

Figure 3:
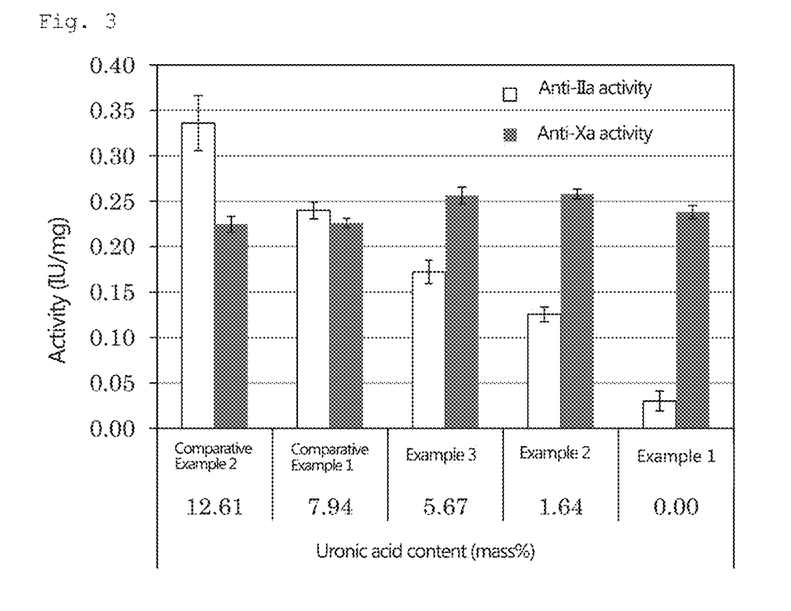
FIG. 3 is a graph showing the relationship between the uronic acid content and the anti-IIa activity or anti-Xa activity of each pentosan polysulfate.
Figure 4:
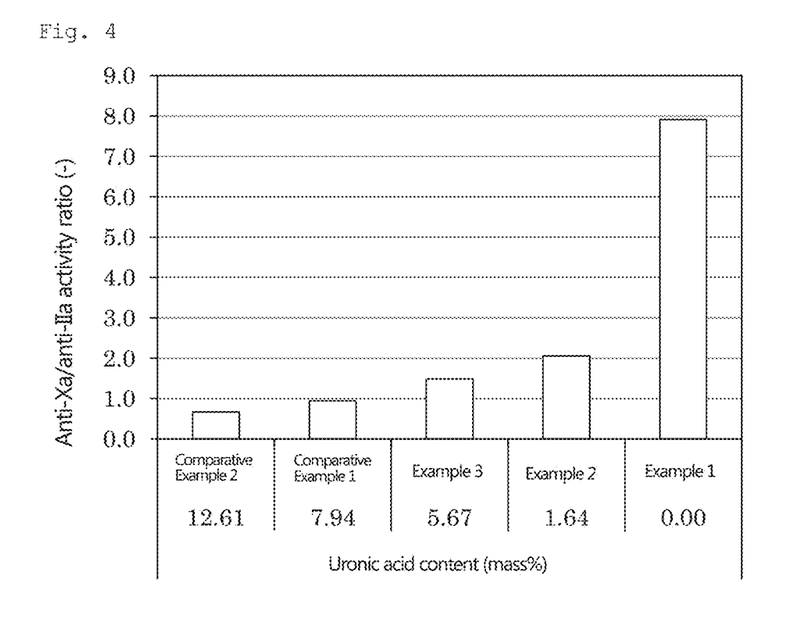
FIG. 4 is a graph showing the relationship between the uronic acid content and the anti-Xa/anti-IIa activity ratio of each pentosan polysulfate.

FIGS. 3 and 4 are graphs showing the relationship between the uronic acid content and the anti-IIa activity, anti-Xa activity, or anti-Xa/anti-IIa activity ratio of each pentosan polysulfate sodium obtained in the above Examples and Comparative Examples.

As can be seen from the results shown in Table 1 and FIG. 4, the lower the uronic acid content, the higher the anti-Xa/anti-IIa activity ratio.

TABLE 2

|  | Comparative Example 2 | Comparative Example 1 | Example 3 | Example 2 | Example 1 |
|---|---|---|---|---|---|
| Yield (g) | 2.40 | 2.24 | 2.89 | 3.02 | 3.85 |

Table 2 shows the yields when pentosan polysulfate sodium powder was obtained from xylooligosaccharide powder. The results of Table 2 clearly show that as the uronic acid content was lower, pentosane polysulfate sodium was obtained in a larger amount (with a higher yield).

Stability 2 mL of a 100 mg/mL aqueous pentosan polysulfate sodium solution was placed in a 5-mL vial, and stored at 40° C. for 4 weeks. The appearance properties of the solution were confirmed.

TABLE 3

|  | Comp. Ex. 2 | Comp. Ex. 1 | Example 3 | Example 2 | Example 1 |
|---|---|---|---|---|---|
| Appearance properties of the solution (initial) | Colorless transparent | Colorless transparent | Colorless transparent | Colorless transparent | Colorless transparent |

TABLE 3-continued

|  | Comp. Ex. 2 | Comp. Ex. 1 | Example 3 | Example 2 | Example 1 |
|---|---|---|---|---|---|
| Appearance properties of the solution (2-week storage at 40° C.) | Slightly yellow transparent | Slightly yellow transparent | Colorless transparent | Colorless transparent | Colorless transparent |

The results of Table 3 clearly show that the aqueous pentosan polysulfate sodium solutions having a high uronic acid content (Comparative Examples 1 and 2) turned yellow after storage at 40° C. for 4 weeks; whereas the aqueous pentosan polysulfate sodium solutions having a low uronic acid content (Examples 1 to 3) exhibited no change, and were stable. This result suggests that the pentosan polysulfate of the present invention (including pentosan polysulfate in other forms, such as a powder) is less susceptible to adverse effects of moisture, and is highly stable.

The invention claimed is:

1. A pentosan polysulfate compound selected from the group consisting of a pentosan polysulfate; a pharmaceutically acceptable salt of the pentosan polysulfate; a pharmaceutically acceptable solvate of the pentosan polysulfate; and a pharmaceutically acceptable solvate of the pharmaceutically acceptable salt of the pentosan polysulfate, wherein the pentosan polysulfate has an acetyl group content of 0 mass % to 2.0 mass % and a uronic acid content of 0.0 mass % to 2.0 mass %.

2. The pentosan polysulfate compound according to claim 1, wherein the pentosan polysulfate has a structure represented by Formula II:

Formula II wherein $R^1$ each independently represents a hydrogen atom, —COCH3, or —$SO_3X^1$, and at least one $R^1$ in the molecule is —$SO_3X^1$, wherein $X^1$ represents a hydrogen atom or a monovalent or divalent metal; n1 and n2 each independently represent an integer of 0 or more and 30 or less, and at least one of n1 and n2 is an integer of 1 or more; and R* represents a hydrogen atom, —COCH3, —SO$_3$X$^1$, or a sulfated or non-sulfated uronic acid residue.

3. The pentosan polysulfate compound according to claim 1, wherein the pentosan polysulfate is represented by Formula I:

Formula I wherein each R independently represents a hydrogen atom, —COCH$_3$ or —SO$_3$X, and at least one R is —SO$_3$X, wherein X represents a hydrogen atom or a monovalent or divalent metal; and n is an integer of 1 or more and 30 or less.

4. The pentosan polysulfate compound according to claim 3, wherein each R independently represents a hydrogen atom or —SO$_3$X.

5. The pentosan polysulfate compound according to claim 3, wherein X is sodium.

6. A pharmaceutical composition comprising the pentosan polysulfate compound according to claim 1 and a pharmaceutically acceptable carrier.

7. An anticoagulant comprising the pentosan polysulfate compound according to claim 1 and a pharmaceutically acceptable carrier.

8. The pentosan polysulfate compound according to claim 1, wherein the pentosan polysulfate has an acetyl group content of 0 mass % to 2.0 mass % and a uronic acid content of 0.0 mass % to 1.0 mass %.

9. A method for producing the pentosan polysulfate compound of claim 1 comprising:
(i) depolymerizing a plant-derived raw material to obtain a neutral xylooligosaccharide, and (ii) sulfating the neutral xylooligosaccharide.

10. The method for producing pentosan polysulfate according to claim 9, wherein the step (i) is performed by heating.

11. The method for producing pentosan polysulfate according to claim 10, wherein the step (i) is performed by heating to 120° C. or higher under non-alkaline conditions.

12. The method for producing pentosan polysulfate according to claim 9, wherein the plant-derived raw material is a wood-derived raw material.

* * * * *